US012773126B2

(12) United States Patent
Qie et al.

(10) Patent No.: US 12,773,126 B2
(45) Date of Patent: Oct. 27, 2026

(54) MOTION DATA COLLECTION DEVICE, METHOD AND APPARATUS, AND WEARABLE DEVICE

(71) Applicant: GOERTEK INC., Weifang (CN)

(72) Inventors: Yong Qie, Weifang (CN); Jinshan Zheng, Weifang (CN); Junjie Pan, Weifang (CN)

(73) Assignee: GOERTEK INC., Weifang (CN)

( * ) Notice: Subject to any disclaimer, the term of this patent is extended or adjusted under 35 U.S.C. 154(b) by 369 days.

(21) Appl. No.: 18/700,309

(22) PCT Filed: Dec. 16, 2021

(86) PCT No.: PCT/CN2021/138713
§ 371 (c)(1),
(2) Date: Apr. 11, 2024

(87) PCT Pub. No.: WO2023/102999
PCT Pub. Date: Jun. 15, 2023

(65) Prior Publication Data

US 2024/0398258 A1 Dec. 5, 2024

(30) Foreign Application Priority Data

Dec. 8, 2021 (CN) ........................ 202111494904.0

(51) Int. Cl.
*A61B 5/11* (2006.01)
*A61B 5/00* (2006.01)

(52) U.S. Cl.
CPC ............... *A61B 5/11* (2013.01); *A61B 5/6802* (2013.01)

(58) Field of Classification Search
CPC ... G06F 8/61; G06F 8/65; G06F 9/445; G06F 1/00; G06F 5/00; G06F 11/00; G06F 9/00;

(Continued)

(56) References Cited

U.S. PATENT DOCUMENTS 4,280,288 A * 7/1981 Corfa ....................... E21C 50/00 37/313
5,799,474 A * 9/1998 Ingram ................ A01D 89/003 56/119

(Continued)

FOREIGN PATENT DOCUMENTS

CN 105388820 A 3/2016
CN 105430061 A 3/2016

(Continued)

OTHER PUBLICATIONS

International Search Report from International Application No. PCT/CN2021/138713 mailed Aug. 29, 2022.

*Primary Examiner* — Daniel Previl
(74) *Attorney, Agent, or Firm* — Shih IP Law Group, PLLC

(57) ABSTRACT

Disclosed in the present disclosure are a motion data collection device, method and apparatus, and a wearable device. The motion data collection device comprises: a fixed portion configured to be fixed on a part of a moving object to be detected; and a collector movably mounted on the fixed portion, wherein the collector comprises a processor, a detection pin group connected to the processor, and a first identification position arranged on a surface of the collector and corresponding to the position of the detection pin group; the fixed portion is provided with a plurality of probe groups, and a plurality of second identification positions arranged corresponding to the positions of the probe groups in a one-to-one correspondence; after the collector is mounted on the fixed portion, when the detection pin group is connected to different probe groups, different detection signals are detected.

10 Claims, 4 Drawing Sheets

(58) Field of Classification Search

CPC .......... G06F 15/00; G06F 13/00; G06F 17/00; G06F 16/00; G06F 2111/00; G06F 2101/00; G06F 40/00; G06F 2206/00; G06F 2205/00; G06F 2203/00; G06N 5/022; G06N 7/01; G06N 3/00; G06N 5/00; G06N 7/00; G06N 10/00; G06N 20/00; G06N 99/00; G06Q 10/067; G06Q 10/20; G06Q 20/14; G06Q 30/018; G06Q 30/0202; G06Q 30/0206; G06Q 30/0283; G06Q 30/04; G06Q 30/08; G06Q 40/00; G06Q 40/02; G06Q 40/04; G06Q 40/12; G06Q 50/06; G06Q 10/00; G06Q 20/00; G06Q 30/00; G06Q 50/00; G06Q 90/00; G06Q 99/00; G06Q 2220/00; G06Q 2230/00; G06Q 2240/00; G06Q 2250/00; H04L 67/34; H04L 1/00; H04L 5/00; H04L 7/00; H04L 9/00; H04L 12/00; H04L 13/00; H04L 2201/00; H04L 2101/00; H04L 69/00; H04L 67/00; H04L 65/00; H04L 63/00; H04L 61/00; H04L 2212/00; H04L 2209/00; H04L 2203/00; H05B 47/10; H05B 47/11; H05B 47/19; H05B 47/1965; H05B 1/00; H05B 3/00; H05B 6/00; H05B 7/00; H05B 11/00; H05B 33/00; H05B 35/00; H05B 39/00; H05B 41/00; Y02B 20/40; Y02P 90/84; Y02P 90/90; A61B 5/11; A61B 5/6802; G06T 2207/10016; G06T 2207/10028; G06T 2207/30241; G06T 2207/30244; G06T 7/20; G06T 7/70; G06T 7/73; G06V 10/62; G06V 20/10; G06V 20/44; G06V 40/28; G06V 10/00; G06V 20/00; G06V 30/00; G06V 40/00; G06V 2201/00

USPC .... 340/427, 426.2, 438, 454, 463, 472, 471, 340/488, 539.22, 546

See application file for complete search history.

(56) References Cited

U.S. PATENT DOCUMENTS

| | | | | |
|---|---|---|---|---|
| 2010/0070316 | A1* | 3/2010 | Lieberman | A43B 3/46 701/469 |
| 2012/0116548 | A1* | 5/2012 | Goree | A61B 5/7253 700/90 |
| 2013/0346229 | A1* | 12/2013 | Martin | G06F 8/61 705/35 |
| 2019/0208384 | A1* | 7/2019 | Matus | G01S 19/42 |
| 2020/0348662 | A1* | 11/2020 | Cella | G05B 13/028 |
| 2022/0108262 | A1* | 4/2022 | Cella | G01N 29/14 |
| 2023/0360254 | A1* | 11/2023 | Liu | G06T 7/70 |
| 2023/0401274 | A1* | 12/2023 | Denninghoff | G06F 16/9538 |

FOREIGN PATENT DOCUMENTS

| | | | |
|---|---|---|---|
| CN | 106771417 | A | 5/2017 |
| CN | 106815556 | A | 6/2017 |
| CN | 206325193 | U | 7/2017 |
| CN | 110141221 | A | 8/2019 |
| CN | 210924958 | U | 7/2020 |
| CN | 213875871 | U | 8/2021 |
| CN | 217014031 | U | 7/2022 |
| EP | 3869478 | A1 | 8/2021 |
| JP | H1170109 | A | 3/1999 |

* cited by examiner

MOTION DATA COLLECTION DEVICE, METHOD AND APPARATUS, AND WEARABLE DEVICE

The present disclosure claims the priority to the Chinese Patent Application No. 202111494904.0, entitled "MOTION DATA COLLECTION DEVICE, METHOD AND APPARATUS, AND WEARABLE DEVICE" filed with China Patent Office on Dec. 8, 2021, the entire contents of which are incorporated into the present disclosure by reference.

Technical Field

The present disclosure relates to a technical field of wearable devices, and more particularly, to a motion data collection device, a motion data collection method and a motion data collection apparatus, and a wearable device.

Description of Related Art

With economic growth and improvement in living standards, more and more people are passionate about physical motion and pay attention to detailed data about their own motions. Intelligent motion data collection terminals are increasingly appearing in people's daily lives, bringing convenience to everyone. At present, these collection terminals are generally applied in a single scenario, some are worn on different parts of the human body, such as shoes, the wrist, the belt, etc., to collect motion data; some are installed on different instruments to collect corresponding motion data, for example installed on bicycle wheels, racket handles to collect motion data; etc. Users need to use different special collection terminals in different motion modes, which is very inconvenient.

In view of this, how to provide a motion data collection device, motion data collection method and motion data collection apparatus, and a wearable device that can integrate a plurality of motion modes has become a problem that those skilled in the art need to solve.

SUMMARY

A purpose of embodiments of the present disclosure is to provide a motion data collection device, a motion data collection method and a motion data collection apparatus, and a wearable device, the present invention can be applied to various types of motion and various motion scenarios during use, especially applicable for wearable devices such as smart watches, the present invention is widely applicable and flexible to use, bringing convenience to users.

In order to achieve the above purpose, an embodiment of the present disclosure provides a motion data collection device, including a fixed portion configured to be fixed on a part, to be detected, of a moving object, and a collector movably mounted on the fixed portion, wherein the collector includes a processor, a detection pin group connected to the processor, and a first identification position arranged on a surface of the collector and corresponding to the position of the detection pin group; the fixed portion is provided with a plurality of probe groups, and a plurality of second identification positions arranged corresponding to the positions of the probe groups in a one-to-one correspondence;

- after the collector is mounted on the fixed portion, when the detection pin group is connected to different probe groups, different detection signals are detected; the processor is used for acquiring a current detection signal detected by the detection pin group, determining a target motion type according to the current detection signal and a pre-established correspondence relationship between a motion type and a detection signal, and collecting motion data corresponding to the target motion type.

Optionally, the detection pin group includes m detection pins, the probe group includes m probes, and an arrangement of the m detection pins is the same as an arrangement of the m probes, so that when the detection pin group is connected to the probe group, ports of the detection pins are connected to the probes in the probe group in a one-to-one correspondence, and a corresponding detection signal is detected, wherein the m is not less than 3.

Optionally, the detection pin group includes one power pin, one ground pin and m−2 identification pins; each of the probe groups includes one power probe, one ground probe and m−2 identification probes, probes in each of the probe groups are connected in different connection manners respectively, so that different voltage combination signals are detected when the detection pin group is connected to different probe groups respectively; wherein

- when the detection pin group is connected to the probe group, the power probe is connected to the power pin, the ground probe is connected to the ground pin, and each of the identification probes is connected to a corresponding identification pin.

Optionally, a total number of the probe groups is no more than $2^{(m-2)}$.

Optionally, when the m equals to 3, the identification probes are connected to the power probe in a first probe group, and the identification probes are connected to the ground probe in a second probe group;

- accordingly, when the detection pin group is connected to the first probe group, the detected detection signal is high level; and when the detection pin group is connected to the second probe group, the detected detection signal is low level.

Optionally, when the m equals to 4, a first identification probe and a second identification probe are both connected to the power probe in a first probe group, a first identification probe is connected to the power probe and a second identification probe is connected to the ground probe in a second probe group, a first identification probe in a third probe group is connected to the ground probe, a second identification probe is connected to the power probe in a third probe group, and a first identification probe and a second identification probe are both connected to the ground probe in a fourth probe group.

Optionally, the collector has a shape of a round cake, and an installation region located on the fixed portion and corresponding to the collector has a shape matching to the collector.

An embodiment of the present disclosure also provides a motion data collection method applied to the collector as described above, including:

- acquiring a current detection signal detected by the detection pin group;
- determining a target motion type according to the current detection signal and a pre-established correspondence relationship between motion types and the detection signals; and
- collecting motion data corresponding to the target motion type.

Optionally, the acquiring a current detection signal detected by the detection pin group includes:

acquiring a current detection signal detected by the detection pin group after a turning-on signal is detected.

An embodiment of the present disclosure further provides a motion data collection apparatus, which is applied to the collector as described above, including:

an acquisition module configured to acquire a current detection signal detected by the detection pin group;

a matching module configured to determine a target motion type according to the current detection signal and a pre-established correspondence relationship between motion types and detection signals; and a collection module configured to collect motion data corresponding to the target motion type.

An embodiment of the present disclosure further provides a wearable device, including the motion data collection device as described above.

Embodiments of the present disclosure provide a motion data collection device, a motion data collection method and a motion data collection apparatus, and a wearable device, wherein the motion data collection device includes: a fixed portion configured to be fixed on a part, to be detected, of a moving object; and a collector movably mounted on the fixed portion, wherein the collector includes a processor, a detection pin group connected to the processor, and a first identification position arranged on a surface of the collector and corresponding to the position of the detection pin group, the fixed portion is provided with a plurality of probe groups, and a plurality of second identification positions arranged corresponding to the positions of each of the probe groups in a one-to-one correspondence; wherein after the collector is mounted on the fixed portion, when the detection pin group is connected to different probe groups, different detection signals are detected; the processor is configured to acquire a current detection signal detected by the detection pin group, determine a target motion type according to the current detection signal and a pre-established correspondence relationship between motion types and the detection signals, and collect motion data corresponding to the target motion type.

It can be seen that, it can be configured that, when the user needs to monitor the motion data of a certain type of motion to be monitored, the fixed portion is fixed on a part, to be detected, of a moving object, then the collector is mounted on the fixed portion, and the first identification position of the collector is arranged to correspond to a second identification position of the motion type, to be monitored, on the fixed portion, and the collector detects a probe group at the second identification position through the detection pin group to obtain a current detection signal, and then the processor determines a target motion type selected by the user according to the current detection signal and the pre-established correspondence relationship between a motion type and a detection signal, thereby collecting motion data corresponding to the target motion type. The present invention can be applied to various types of motion and various motion scenarios, especially applicable to wearable devices such as smart watches, the present invention is widely applicable and flexible to use, bringing convenience to users.

BRIEF DESCRIPTION OF DRAWINGS

In order to more clearly illustrate technical solutions in the embodiments of the present disclosure, the drawings required to be used for the embodiments or the prior art will be briefly introduced in the following. Obviously, the drawings in the following description are merely a part of the drawings of the present disclosure, and for those of ordinary skill in the art, other drawings can also be obtained from the provided drawings without any creative effort.

DETAILED DESCRIPTIONS

Embodiments of the present disclosure provide a motion data collection device, a motion data collection method and a motion data collection apparatus, and a wearable device, the present invention can be applied to various types of motion and various motion scenarios during use, especially applicable for wearable devices such as smart watches, is widely applicable and flexible to use, bringing convenience to users.

In order to make the purpose, technical solutions and advantages of embodiments of the present disclosure clearer, the technical solutions of embodiments of the present disclosure will be clearly and completely described below with reference to the drawings in the embodiments of the present disclosure. Obviously, the described embodiments are only a part of the embodiments of the present disclosure, rather than all the embodiments. Based on the embodiments in the present disclosure, all other embodiments obtained by those of ordinary skill in the art without creative efforts shall fall within the protection scope of the present disclosure.

Figure 1:
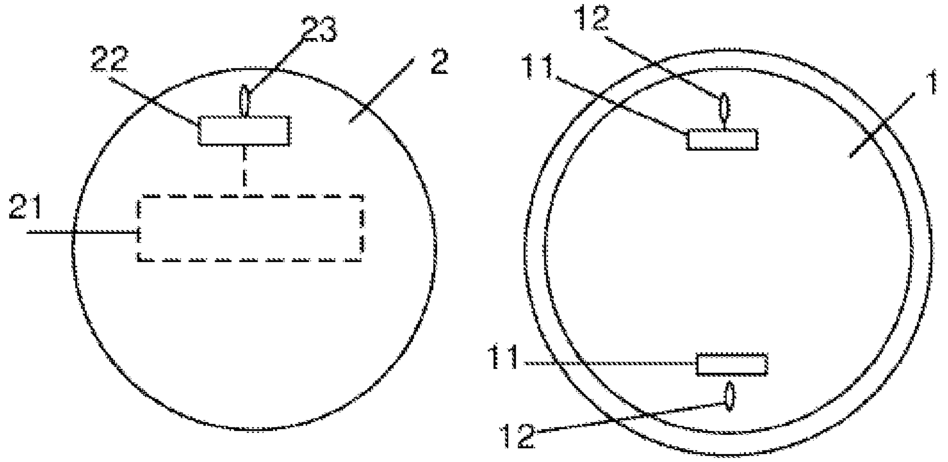
FIG. 1 is a schematic structural diagram of a motion data collection device according to an embodiment of the present disclosure.

Referring to FIG. 1, FIG. 1 is a schematic structural diagram of a motion data collection device according to an embodiment of the present disclosure. The motion data collection device includes a fixed portion 1 configured to be fixed on a part, to be detected, of a moving object, and a collector 2 movably mounted on the fixed portion 1, the collector 2 includes a processor 21, a detection pin group 22 connected to the processor 21, and a first identification position 23 arranged on a surface of the collector 2 and corresponding to the position of the detection pin group 22; the fixed portion 1 is provided with a plurality of probe groups 11, and a plurality of second identification positions 12 arranged corresponding to the positions of each of the probe groups 11 in a one-to-one correspondence, and each identification position 12 corresponds to a part to be detected;

after the collector 2 is mounted on the fixed portion 1, when the detection pin group 22 is connected to different probe groups 11, different detection signals are detected; the processor 21 is used for acquiring a current detection signal detected by the detection pin group 22, determining a target motion type according to the current detection signal and a pre-established correspondence relationship between motion types and detection signals, and collecting motion data corresponding to the target motion type.

It should be noted that the motion data collection device in the embodiment of the present disclosure includes a fixed portion 1 and a collector 2, and during use, the fixed portion 1 is used to be fixed on a part of a moving object to be detected, such as the wrist or waist of the human body, the collector 2 can be detachably fixed on the fixed portion 1, a plurality of probe groups 11 are provided in the fixed portion 1, and second identification positions 12 corresponding to corresponding each of the probe groups 11 respectively are arranged on a surface of the fixed portion 1. Specifically, the second identification position 12 may be a motion type identification, that is, a plurality of motion type identifications are provided. The collector 2 is provided with a processor 21 and a detection pin group 22 connected to the processor 21 therein, and a first identification position 23 corresponding to the detection pin group 22 is arranged on a surface of the collector 2. Here, the purpose of providing the first identification position 23 and the second identification position 12 is to enable users to align the first identification position 23 of the collector 2 with the second identification position 12 of the probe group 11 that needs to be detected on the fixed portion 1 according to actual needs after mounting the collector 2 on the fixed portion 1, so that the detection pin group 22 on the collector 2 can generate a detection signal corresponding to one connected probe group 11 after the collector 2 is fixed on the fixed portion 1, and since the detection pin group 22 generates different detection signals when it is connected to different probe groups 11, a correspondence relationship between a detection signal and a motion type can be established in advance. Accordingly, users can mount the collector 2 on the fixed portion 1 according to a required motion type, so that the first identification position 23 on the collector 2 is aligned with the second identification position 12 corresponding to the part to be detected on the fixed portion 1; at this time, the detection pin group 22 is connected to the probe group 11 at the second identification position 12 to generate a corresponding detection signal, and the processor 21 detects the current detection signal and then determines a target motion type according to the current detection signal and the pre-established correspondence relationship between a motion type and a detection signal, and collects corresponding motion data by calling a data acquisition program corresponding to the target motion type. Here, the data acquisition program corresponding to each motion type can be stored in the processor in advance, so that after the target motion type is determined, the corresponding data acquisition program can be directly called to collect motion data. In addition, a corresponding App can also be operated on a host computer such as a mobile phone. Here, after the App establishes a connection with the motion data collection device, motion data information containing motion category identification codes and sent by the motion data collection device can be received.

Specifically, after the user installs the collector 2 on the fixed portion 1, a collection switch can be turned on (specifically, turned on by a switch button or touch), and the processor 21 starts to operate and detects the current detection signal.

It should also be noted that the part to be detected in the embodiment of the present disclosure may be one or more of the wrist, foot, waist, tennis, badminton, boat, bicycle, fencing, etc., and can be determined according to actual situations, and it is not particularly limited in the embodiment of the present disclosure. Each second identification position 12 in the embodiment of the present disclosure may specifically use a keyword corresponding to the part to be detected, or may be a pattern corresponding to the part to be detected, and in order to enable the user to more accurately align the first identification position 23 with the corresponding second identification position 12, the first identification position 12 in the present disclosure may be an arrow, and it also possible to provide a corresponding arrow at the second identification position 12, so that the user can align the arrow on the collector 2 with the arrow at the corresponding second identification position 12 when mounting the collector 2 on the fixed portion 1. Of course, the specific manner to indicate the first identification position 23 and the second identification position 12 can be determined according to actual situations, and it is not particularly limited in the present disclosure.

Furthermore, referring to FIGS. 2-5, the detection pin group 22 in the embodiment of the present disclosure includes m detection pins A, the probe group 11 includes m probes B, and the arrangement of the m detection pins A is the same as the arrangement of the m probes B, so that when the detection pin group 22 is connected to the probe group 11, the port of each of the detection pins A is connected to each of the probes B in the probe group 11 in a one-to-one correspondence, and a corresponding detection signal is detected, wherein m is not less than 3.

Specifically, in the embodiment of the present disclosure, the number of detection pins A in the detection pin group 22 is the same as the number of probes B in the probe group 11, so that when the detection pin group 22 is aligned with one of the probe groups 11, the port of the detection pins A is connected to each probe B in the probe group 11 in a one-to-one correspondence, and a corresponding detection signal is generated.

Furthermore, the detection pin group 22 includes a power pin V, a ground pin G and m−2 identification pins ID; each of the probe groups 11 includes a power probe BV, a ground probe BG and m−2 identification probes BID, probes B in the probe groups 11 are connected in different: connection manners respectively, so that different voltage combination signals can be detected when the detection pin group 22 is connected to different probe groups 11 respectively;

wherein when the detection pin group 22 is connected to the probe group 11, the power probe BV is connected to the power pin V, the ground probe BG is connected to the ground pin G, and each identification probe BID is connected to a corresponding identification pin ID.

It should be noted that in the embodiment of the present disclosure, the position and size of one power pin V, one ground pin G and m−2 identification pins ID in the detection pin group 22 are exactly the same as the position and size of one power probe BV, one ground probe BG and m−2 identification probes BID. Here, in order to ensure that different voltage combination signals are generated when each probe group 11 is connected to the detection pin group 22, each probe B in each probe group 11 may have different connection manners.

Furthermore, in the embodiment of the present disclosure, a total number of the probe groups 11 is no more than $2^{(m-2)}$.

Furthermore, when the m equals to 3, the identification probes BID1 are connected to the power probe BV1 in a first probe group 11, and the identification probes BID2 are connected to the ground probe BG2 in a second probe group 11;

accordingly, when the detection pin group 22 is connected to the first probe group, the detected detection signal is high level; and when the detection pin group is connected to the second probe group, the detected detection signal is low level.

Figure 2:
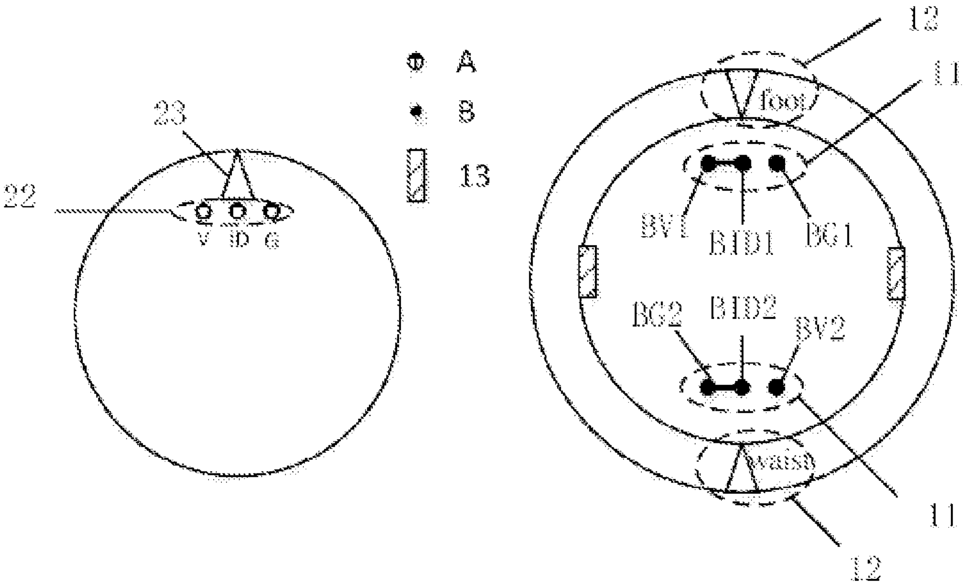
FIG. 2 is a schematic structural diagram of a collector and a fixed portion according to an embodiment of the present disclosure.

Specifically, as illustrated in FIG. 2, the detection pin group includes three pins, among them, including one identification pin. Specifically, the identification probe BID1 in the first probe group 11 is connected to the power probe BV1, that is, a high level signal is generated; the identification probe BID2 in the second probe group 11 is connected to the ground probe BG2, that is, a low level signal is generated. Therefore, a correspondence relationship between the motion type and high and low levels can be established according to specifically generated high and low levels. For example, after the user mounts the collector 2 on the fixed portion 1, the processor 21 detects a corresponding voltage combination signal. For example, when it is detected that the identification probe BID1 is at high level, it means that the first identification position 23 of the collector 2 is aligned with the second identification position 12 corresponding to the first probe group 11 on the fixed portion 1, so that the motion type corresponding to the high level can be determined, thereby a corresponding data acquisition program can be called to collect the corresponding motion data.

Figure 3:
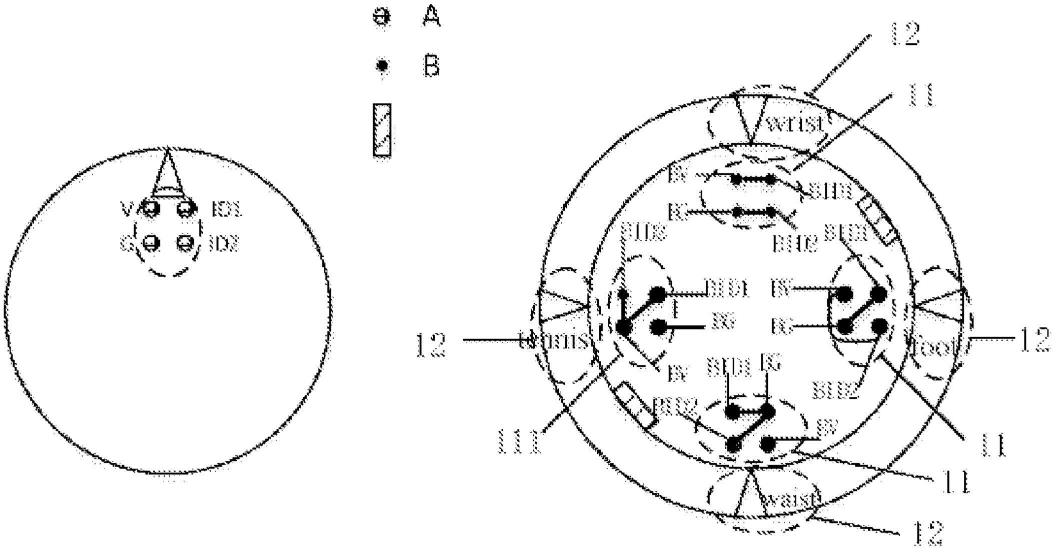
FIG. 3 is a schematic structural diagram of a collector and a fixed portion according to another embodiment of the present disclosure.

Furthermore, as illustrated in FIG. 3, when the m equals to 4, the first identification probe BID1 and the second identification probe BID2 are both connected to the power probe BV in the first probe group 11, the first identification probe BID1 is connected to the power probe BV in the second probe group 11, the second identification probe BID2 is connected to the ground probe BG in the second probe group 11, the first identification probe BID1 is connected to the ground probe BG in the third probe group 11, the second identification probe BID2 is connected to the power probe BV in the third probe group 11, and the first identification probe BID1 and the second identification probe BID2 are both connected to the ground probe BG in the fourth probe group 11.

Specifically, in the embodiment of the present disclosure, the fixed portion is designed with respect to four motion types, and four pins, including 2 detection pins ID, need to be provided on the collector 2. In practical applications, data can be collected for each of the four motion types.

Figure 4:
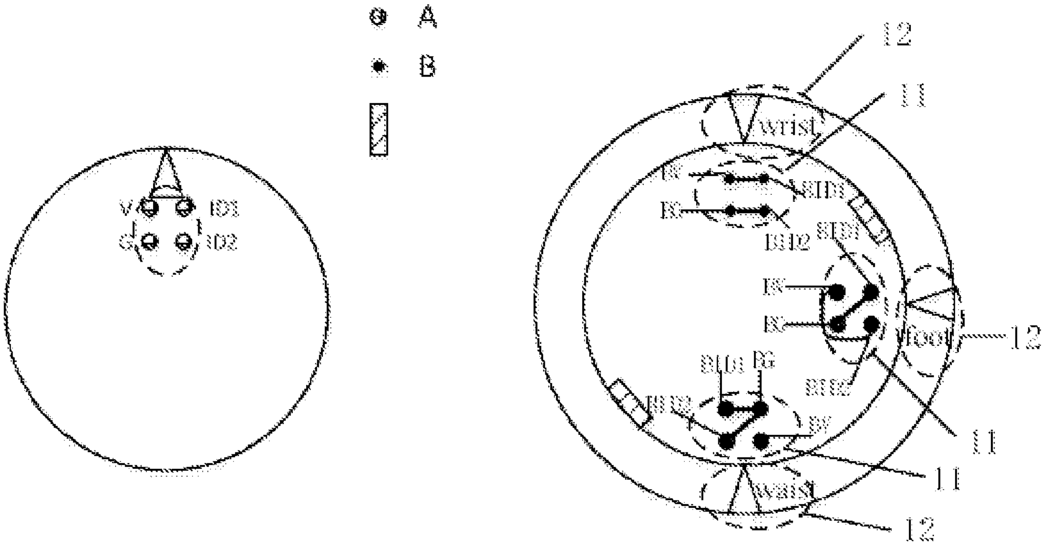
FIG. 4 is a schematic structural diagram of a collector and a fixed portion according to still another embodiment of the present disclosure.
Figure 5:
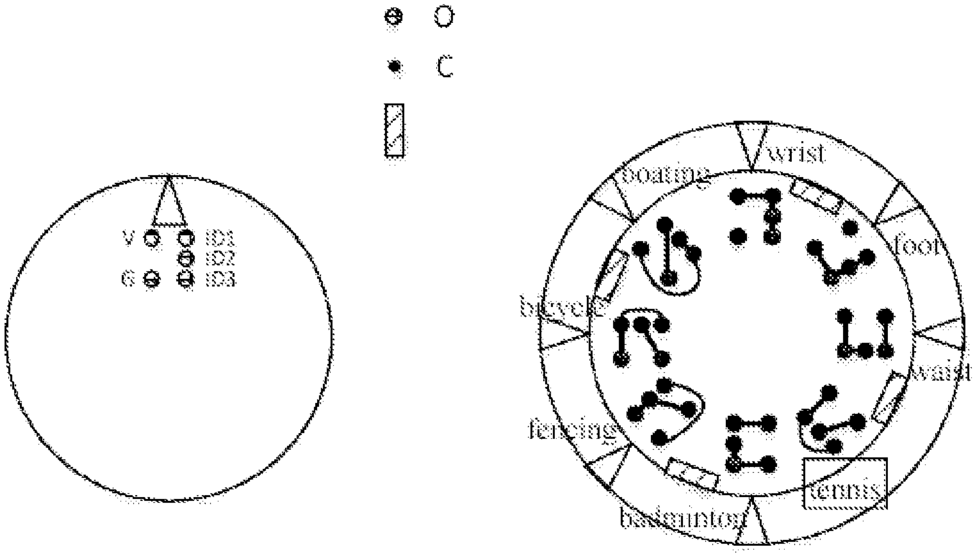
FIG. 5 is a schematic structural diagram of a collector and a fixed portion according to yet another embodiment of the present disclosure.

Of course, as illustrated in FIG. 4, it also can design a corresponding fixed portion 1 with respect to three motion types. Specifically, three probe groups can be randomly selected from the above four probe groups to form the fixed portion 1; the specific selection of probe groups can be determined according to actual situations, and it is not particularly limited in the embodiment of the present disclosure.

It should be noted that, in actual applications, the specific value of m can be determined according to the number of motion types that need to be detected. For example, in the case where eight motion types need to be detected, three identification pins ID are required, m=5, and each probe group on the fixed portion includes five probes. The connection manner of each probe in each probe group can be referred to FIG. 5. Of course, if more motion types are needed to be detected, the specific value of m can be determined according to actual needs, and then the connection manner of each probe in each probe group can be determined according to the number of probes in each group.

Specifically, in the embodiment of the present disclosure, the collector 2 may be in a shape of a round cake (or a button shape), and the shape of an installation region located on the fixed portion 1 and corresponding to the collector 2 matches the shape of the collector 2, so that the collector 2 can be installed on the installation region of the fixed portion 1. In addition, a mounting groove may be provided on the fixed portion 1, so that the collector 2 can be rotated to the corresponding second identification position through the mounting groove when the collector 2 is installed on the fixed portion 1.

It can be seen that, when the user needs to monitor the motion data of a certain motion type to be monitored, the fixed portion can be fixed on a part of the moving object to be detected, then the collector is mounted on the fixed portion, and the first identification position of the collector is arranged to correspond to the second identification position for the motion type to be monitored on the fixed portion, and the collector detects the probe group at the second identification position by the detection pin group to obtain the current detection signal, and then the processor determines a target motion type selected by the user according to the current detection signal and the pre-established correspondence relationship between the motion type and the detection signal, thereby collecting motion data corresponding to the target motion type. The present disclosure can be applied to various motion types and various motion scenarios, especially suitable for wearable devices such as smart watches, is widely applicable and flexible to use, bringing convenience to users.

Figure 6:
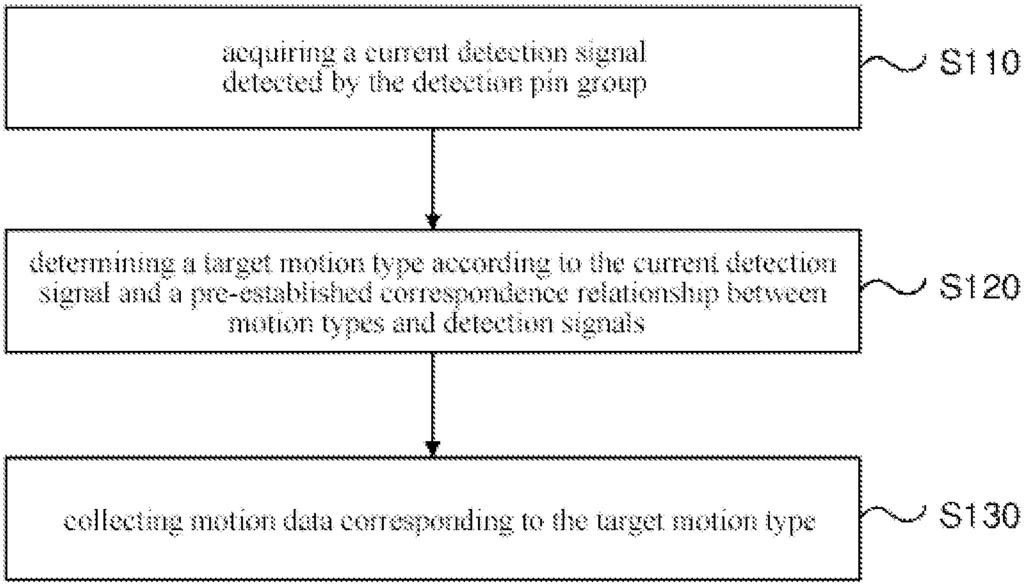
FIG. 6 is a schematic flow chart of a motion data collection method according to an embodiment of the present disclosure.

On the basis of the above embodiments, an embodiment of the present disclosure also provides a motion data collection method applied to the collector as described d above, in particular, referring to FIG. 6. The motion data collection method includes:

S110: acquiring a current detection signal detected by the detection pin group;

S120: determining a target motion type according to the current detection signal and a pre-established correspondence relationship between motion types and detection signals; and S130: collecting motion data corresponding to the target motion type.

Furthermore, in particular, acquiring a current detection signal detected by the detection pin group in S110 includes:

acquiring the current detection signal detected by the detection pin group after an on signal is detected.

It should be noted that the motion data collection method provided in the embodiment of the present disclosure has the same beneficial effects as the motion data collection device provided in the above embodiments, and for the specific descriptions of the collector involved in the embodiments of the present invention, please refer to the above embodiments, and will not be repeated herein.

Figure 7:
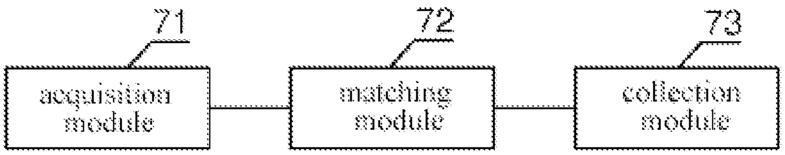
FIG. 7 is a schematic structural diagram of a motion data collection apparatus according to an embodiment of the present disclosure.

On the basis of the above embodiments, referring to FIG. 7, an embodiment of the present disclosure also provides a motion data collection apparatus applied to the collector as described above. The motion data collection apparatus includes:

an acquisition module 71 configured to acquire a current detection signal detected by the detection pin group;

a matching module 72 configured to determine a target motion type according to the current detection signal and a pre-established correspondence relationship between motion types and detection signals; and a collection module 73 configured to collect motion data corresponding to the target motion type.

It should be noted that the motion data collection apparatus provided in the embodiment of the present disclosure has the same beneficial effects as the motion data collection method provided in the above embodiments, and for the specific descriptions of the motion data collection method involved in the embodiments of the present invention, please refer to the above embodiments, and will not be repeated herein.

On the basis of the above embodiments, an embodiment of the present disclosure also provides a wearable device, including the above-mentioned motion data collection device.

The various embodiments in the present specification are described in a progressive manner, and each embodiment focuses on the differences from other embodiments, and the same and similar parts between the various embodiments can be referred to each other. As for the device disclosed in the embodiment, since it corresponds to the method disclosed in the embodiment, the description is relatively simple. For relevant parts, please refer to the description of the method.

It should be noted that relational terms such as first and second described herein are only used to distinguish one entity or operation from another entity or operation, and do not necessarily require or imply any such actual relationship or order between these entities or operations. Moreover, terms such as "comprise", "include" or any other variation thereof are intended to encompass a non-exclusive inclusion such that a process, method, article or apparatus that includes a series of elements includes not only those elements, but also other elements not explicitly listed, or elements inherent to such a process, method, article or apparatus. Without further limitation, the element defined by the phrase "comprising a . . . " does not preclude the presence of additional identical elements in the process, method, article or apparatus including the element.

The above description of the disclosed embodiments enables any person skilled in the art to implement or make use of the present disclosure. Various modifications to these embodiments will be readily apparent to those skilled in the art, and the generic principles defined herein may be implemented in other embodiments without departing from the spirit or scope of the present disclosure. Therefore, this application is not intended to be limited to the embodiments shown herein, but is to be accorded the widest scope consistent with the principles and novel features disclosed herein.

What is claimed is:

1. A motion data collection device, comprising a fixed portion configured to be fixed on a part to be detected of a moving object and a collector movably mounted on the fixed portion, wherein the collector includes a processor, a detection pin group connected to the processor, and a first identification position arranged on a surface of the collector and corresponding to a position of the detection pin group; the fixed portion is provided with a plurality of probe groups and a plurality of second identification positions arranged corresponding to positions of the probe groups in a one-to-one correspondence, and each of the second identification positions corresponds to one portion to be detected, wherein after the collector is mounted on the fixed portion, when the detection pin group is connected to different probe groups, different detection signals are detected; the processor is configured to acquire a current detection signal detected by the detection pin group, determine a target motion type according to the current detection signal and a pre-established correspondence relationship between motion types and the detection signals, and collect motion data corresponding to the target motion type.

2. The motion data collection device of claim 1, wherein the detection pin group comprises m detection pins, the probe group comprises m probes, and an arrangement of the m detection pins is the same as an arrangement of the m probes, so that when the detection pin group is connected to the probe group, ports of the detection pins are connected to the probes in the probe group in a one-to-one correspondence, and a corresponding detection signal is detected, wherein the m is not less than 3.

3. The motion data collection device of claim 2, wherein the detection pin group comprises one power pin, one ground pin and m−2 identification pins; each of the probe groups comprises one power probe, one ground probe and m−2 identification probes, probes in each of the probe groups are connected in different connection manners respectively, so that different voltage combination signals are detected when the detection pin group is connected to different probe groups respectively, wherein when the detection pin group is connected to the probe group, the power probe is connected to the power pin, the ground probe is connected to the ground pin, and each of the identification probes is connected to a corresponding identification pin.

4. The motion data collection device of claim 3, wherein a total number of the probe groups is no more than $2^{(m-2)}$.

5. The motion data collection device of claim 4, wherein when the m equals to 3, the identification probes are connected to the power probe in a first probe group, and the identification probes are connected to the ground probe in a second probe group, accordingly, when the detection pin group is connected to the first probe group, the detected detection signal is high level; and when the detection pin group is connected to the second probe group, the detected detection signal is low level.

6. The motion data collection device of claim 4, wherein when the m equals to 4, a first identification probe and a second identification probe are both connected to the power probe in a first probe group, a first identification probe is connected to the power probe and a second identification probe is connected to the ground probe in a second probe group, a first identification probe is connected to the ground probe and a second identification probe is connected to the power probe in a third probe group, and a first identification probe and a second identification probe are both connected to the ground probe in a fourth probe group.

7. The motion data collection device of claim 1, wherein the collector has a shape of a round cake, and an installation region located on the fixed portion and corresponding to the collector has a shape matching to the collector.

8. A motion data collection method applied to the collector according to claim 1, comprising:

acquiring a current detection signal detected by the detection pin group;

determining a target motion type according to the current detection signal and a pre-established correspondence relationship between motion types and detection signals; and collecting motion data corresponding to the target motion type.

9. The motion data collection method of claim 8, wherein the acquiring a current detection signal detected by the detection pin group comprises:

acquiring a current detection signal detected by the detection pin group after an on signal is detected.

10. A motion data collection apparatus applied to the collector according to claim 1, comprising:

an acquisition module configured to acquire a current detection signal detected by the detection pin group;

a matching module configured to determine a target motion type according to the current detection signal and a pre-established correspondence relationship between motion types and detection signals; and a collection module configured to collect motion data corresponding to the target motion type.

* * * * *